US008971990B2

(12) United States Patent
Khan et al.

(10) Patent No.: US 8,971,990 B2
(45) Date of Patent: Mar. 3, 2015

(54) SYSTEMS AND METHODS FOR NONLINEAR ELASTOGRAPHY

(71) Applicants: K. M. K. Genghis Khan, Schenectady, NY (US); Chandra Sekher Yerramalli, Raleigh, NC (US)

(72) Inventors: K. M. K. Genghis Khan, Schenectady, NY (US); Chandra Sekher Yerramalli, Raleigh, NC (US)

(73) Assignee: General Electric Company, Niskayuna, NY (US)

( * ) Notice: Subject to any disclaimer, the term of this patent is extended or adjusted under 35 U.S.C. 154(b) by 138 days.

(21) Appl. No.: 13/725,599

(22) Filed: Dec. 21, 2012

(65) Prior Publication Data

US 2014/0180058 A1    Jun. 26, 2014

(51) Int. Cl.
| | |
|---|---|
| *A61B 5/055* | (2006.01) |
| *A61B 8/08* | (2006.01) |
| *G01R 33/563* | (2006.01) |
| *A61B 5/00* | (2006.01) |
| *A61B 6/00* | (2006.01) |
| *A61B 8/00* | (2006.01) |

(52) U.S. Cl.
CPC .......... *A61B 5/055* (2013.01); *G01R 33/56358* (2013.01); *A61B 8/485* (2013.01); *A61B 8/5207* (2013.01); *A61B 5/0048* (2013.01); *A61B 6/48* (2013.01); *A61B 6/5205* (2013.01); *A61B 8/0825* (2013.01); *A61B 8/085* (2013.01); *A61B 8/467* (2013.01)
USPC .......................................... 600/410; 600/438

(58) Field of Classification Search
USPC ........... 600/410, 438, 443, 449, 587; 382/128
See application file for complete search history.

(56) References Cited

U.S. PATENT DOCUMENTS

| | | | |
|---|---|---|---|
| 6,270,459 B1 | 8/2001 | Konofagou et al. | |
| 6,749,571 B2 | 6/2004 | Varghese et al. | |
| 7,223,241 B2 | 5/2007 | Radulescu | |
| 7,297,116 B2 | 11/2007 | Varghese et al. | |
| 7,318,804 B2 | 1/2008 | Weitzel et al. | |
| 7,601,122 B2 | 10/2009 | Zagzebski et al. | |
| 2010/0134629 A1 | 6/2010 | Lindop et al. | |
| 2011/0060210 A1 | 3/2011 | Ehman | |
| 2014/0094702 A1* | 4/2014 | Kim et al. | 600/438 |

FOREIGN PATENT DOCUMENTS

WO        2012035472 A1    3/2012

OTHER PUBLICATIONS

Wang, Z.G., et al.; "Elastography Method for Reconstruction of Nonlinear Breast Tissue Properties"; International Journal of Biomedical Imaging, 2009, Article ID 406854; pp. 1-9.

* cited by examiner

*Primary Examiner* — Michael Rozanski
(74) *Attorney, Agent, or Firm* — Fletcher Yoder, P.C.

(57) ABSTRACT

Nonlinear elastography systems and methods are provided. The elastography system includes a data acquisition module, such as an imaging device, and associated system control circuitry. The data acquisition module is configured to acquire various data, such as displacement and/or force data, from a material. A nonlinear transfer function is applied to the acquired data to generate information about the material's stiffness. In one implementation, a map representative of the material's stiffness is generated.

20 Claims, 7 Drawing Sheets

US 8,971,990 B2

SYSTEMS AND METHODS FOR NONLINEAR ELASTOGRAPHY

BACKGROUND

The subject matter disclosed herein relates generally to the determination of mechanical properties of a material, and more particularly, to systems and methods related to elastography.

Elastography procedures utilize imaging technologies, such as ultrasound or magnetic resonance imaging (MRI), to determine mechanical properties of human tissue or other suitable media. In general, conventional elastography systems measure internal displacement fields within a tissue in response to a particular applied force. The measured displacement fields are assumed to provide an estimate of strain variation within a target tissue, which is used to identify abnormalities within the tissue. For example, because normal tissues display different mechanical properties than tumors, elastography can be used to identify tumors embedded within soft tissue.

However, current elastography techniques utilize assumptions that may be unrealistic or inappropriate in practice and only provide strain maps, which are not necessarily indicative of the more relevant underlying stiffness, or modulus, of locations within a sample. Furthermore, current elastography techniques may result in poor differentiation between tissues of different modulus, poor detection of small abnormalities, and generally poor quality maps of the target tissue.

BRIEF DESCRIPTION

In some embodiments, a method for elastography is provided, the method including applying a displacement to a surface of a volume of a material, measuring a resulting reactive force on the surface or within the volume of the material, and generating a nonlinear transfer function based on a relationship between the applied displacement and the measured resulting reaction force. In some embodiments, the nonlinear transfer function may have a slope that decreases between a relatively low value of strain and a higher value of strain. In certain embodiments, the generated nonlinear transfer function may be stored within a memory for use in an elastography procedure.

In an embodiment of the present disclosure, a system configured to determine mechanical properties of a material having different regions of stiffness is provided. In some embodiments, the system may include an imaging system configured to acquire displacement field data for a volume of the material. The system may include a circuit configured to access one or more nonlinear transfer functions, and may further include a processor configured to apply at least one nonlinear transfer function to acquired displacement field data to generate a modulus map that provides information about the regions of different stiffness within the volume of the material. In certain embodiments, the one or more nonlinear transfer functions may have a generally downward concave shape.

In some embodiments, a method for determining mechanical properties of a material having different regions of stiffness is provided. The method may include applying a force to a surface of a volume of the material to induce a displacement within the volume of the material, and may further include measuring the displacement within the volume of the material to generate a displacement field map. In certain embodiments, the method may include accessing one or more nonlinear transfer functions having a generally downward concave shape, and applying at least one nonlinear transfer function to the displacement field map to generate a modulus map providing information about the regions of different stiffness within the volume of the material.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Inhomogeneous materials have regions of relatively different mechanical properties, such as regions of relatively different stiffness. Described herein are embodiments of elastography systems and methods that may generally provide information about the stiffness, or modulus, of a material. Furthermore, in certain embodiments, the described systems and methods may generate modulus maps of the material, which may aid in identifying variations or abnormalities located within a volume of the material. In the medical field, such systems and methods may be particularly useful in identifying variations within soft tissue, such as tumors or diseased tissue. For example, a region of normal soft tissue may have a relatively low stiffness, while a tumorous region may have a relatively high stiffness. As described in more detail below, application of a nonlinear transfer function to displacement field data and/or map (e.g., a strain map) may provide modulus information and allow for the generation of modulus maps depicting the relative stiffness of different regions within a sample. Additionally, in some circumstances, force and displacement values may be measured for the sample, and in such cases, application of the nonlinear transfer function can provide modulus values for the various regions within the sample, as discussed below.

The embodiments described herein may be performed by any suitable elastography system. Elastography systems of the present disclosure may include an imaging device, such as an ultrasound system or magnetic resonance imaging (MRI) system, and appropriate processing circuitry. To facilitate explanation, the present disclosure primarily discusses non-linear elastography systems and methods in the context of a system having an ultrasound imaging device. However, it should be understood that the following discussion may also be applicable to any of a wide variety of elastography systems and/or imaging devices. The concepts described below may also be applied outside of the medical field to generate modulus information or estimated modulus and/or modulus maps of any suitable material that displays variations in internal stiffness or composition.

Figure 1:
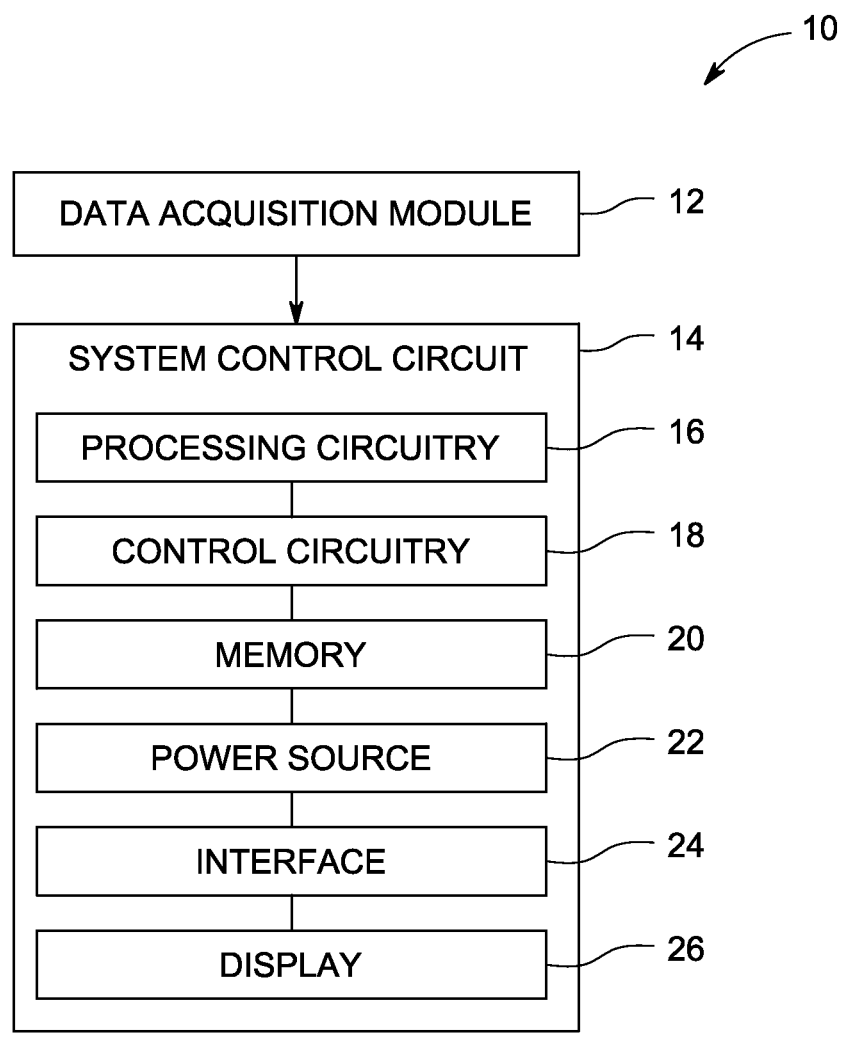
FIG. 1 is a diagrammatic illustration of an embodiment of an elastography system configured to determine a modulus of a material, in accordance with an aspect of the disclosure.

With this in mind, and referring to FIG. 1, an elastography system 10 is illustrated schematically as including a data acquisition module 12 and a system control circuit 14. In general, the data acquisition module 12 is typically an imaging system such as an ultrasound or MRI system, although it is contemplated that the data acquisition module 12 may be any device or system configured to collect displacement and/or force data. In the depicted embodiment, the system control circuit 14 can be generally configured to have processing circuitry 16, control circuitry 18, memory 20, a power source 22, a display 24, and a user interface 26. The data acquisition module 12 and the system control circuit 14 may be integrated into a single platform, or may be directly connected or remotely connected via one or more networks, for example.

In general, the system control circuit 14 may be configured to command operation of the data acquisition module 12 to execute examination protocols and to process acquired data. The system control circuit 14 may additionally or alternatively be configured to receive data, in raw or processed form, from the data acquisition module 12. The system control circuit 14 may then process, store, transmit, or display the data.

In the depicted embodiment, the data acquired by the data acquisition module 12 may be provided to a processing circuitry 16, which may be one or more conventional microprocessors. The system control circuit 14 may have control circuitry 18 which may include a CPU in a multi-purpose or application specific computer or workstation. The control circuitry 18 can be coupled to a memory 20, which may be a structure or circuit that can store programming code for operation of the elastography system and store raw or processed data for later processing, display, and/or transmission. The memory 20 may include one or more optical, magnetic, and/or solid state memory storage structures.

Additionally, the system control circuit 14 may be configured to receive commands and scanning parameters from an operator via an interface 24, typically equipped with a keyboard and/or other input devices. In the illustrated embodiment, a display 26 may be coupled to the interface 24. Additionally, the acquired data or generated images may also be printed by a printer which may be connected to the system control circuit 14. Furthermore, the system control circuit 14 may be connected to other various output devices, such as standard or special computer monitors and associated processing circuitry. Additional displays, interfaces, and associated accessories may be further linked to the system. In general, connections between the data acquisition module 12, system control circuit 14, and any output devices and associated accessories may be direct connections, wireless connections, or any remote connections, such as over one or more networks, and so forth.

It should be further noted that the interface may also be coupled to a picture archiving and communications system (PACS). PACS may in turn be coupled to a remote client, radiology department information system (RIS), hospital information system (HIS), or to an internal or external network, so that others at different locations may gain access to the raw or processed image data.

While FIG. 1 and the preceding discussion generally treat the various components of the described embodiments of the system control circuit 14 together, these various components may be provided in separate platforms or arranged and connected in any suitable manner. For example, one or more of the processing circuitry 16, control circuitry 18, memory 20, power source 22, interface 24, and display 26 may be arranged in various separate platforms or provided within a general or special purpose computer. Furthermore, one or more of the processing circuitry 16, control circuitry 18, memory 20, power source 22, interface 24, and display 26 may be provided in a platform with the data acquisition module 12.

As mentioned above, any suitable data acquisition module 12 may be used as part of the elastography system 10. In certain embodiments, the data acquisition module 12 may include an ultrasound system 40, such as the system depicted in FIG. 2. The depicted embodiment includes an ultrasound probe 42 (hereinafter, "the probe") and a console 44. In the illustrated ultrasound system 40, the probe 42 includes a transducer array 46 having a plurality of transducer elements 48, a transmitter 50, and a receiver 52. The transducer array 46 of the probe 42 can be positioned on a patient 54 and may be manipulated to probe the patient's anatomy via ultrasound signals. In general, the ultrasound system 40 can convert reflected ultrasound signals to an electrical signal when received by a transducer, and the electrical signal may be processed and/or combined with additional electrical signals before being transferred to the console 44.

Further, the probe 42 may be coupled to the console 44. The probe 42 and console 44 may be within a single housing, or may be coupled together through a cable or a wireless connection, for example. The console 44 may include a system control circuit 14, as described above with respect to elastography systems generally. For example, the system control circuit 14 can transmit control signals to the probe 42. By way of another example, the system control circuit 14 can receive digital data, or processed versions of such data, representing reflection signals returned from tissue interfaces within the patient 54 during a pulse-echo data acquisition procedure.

Figure 2:
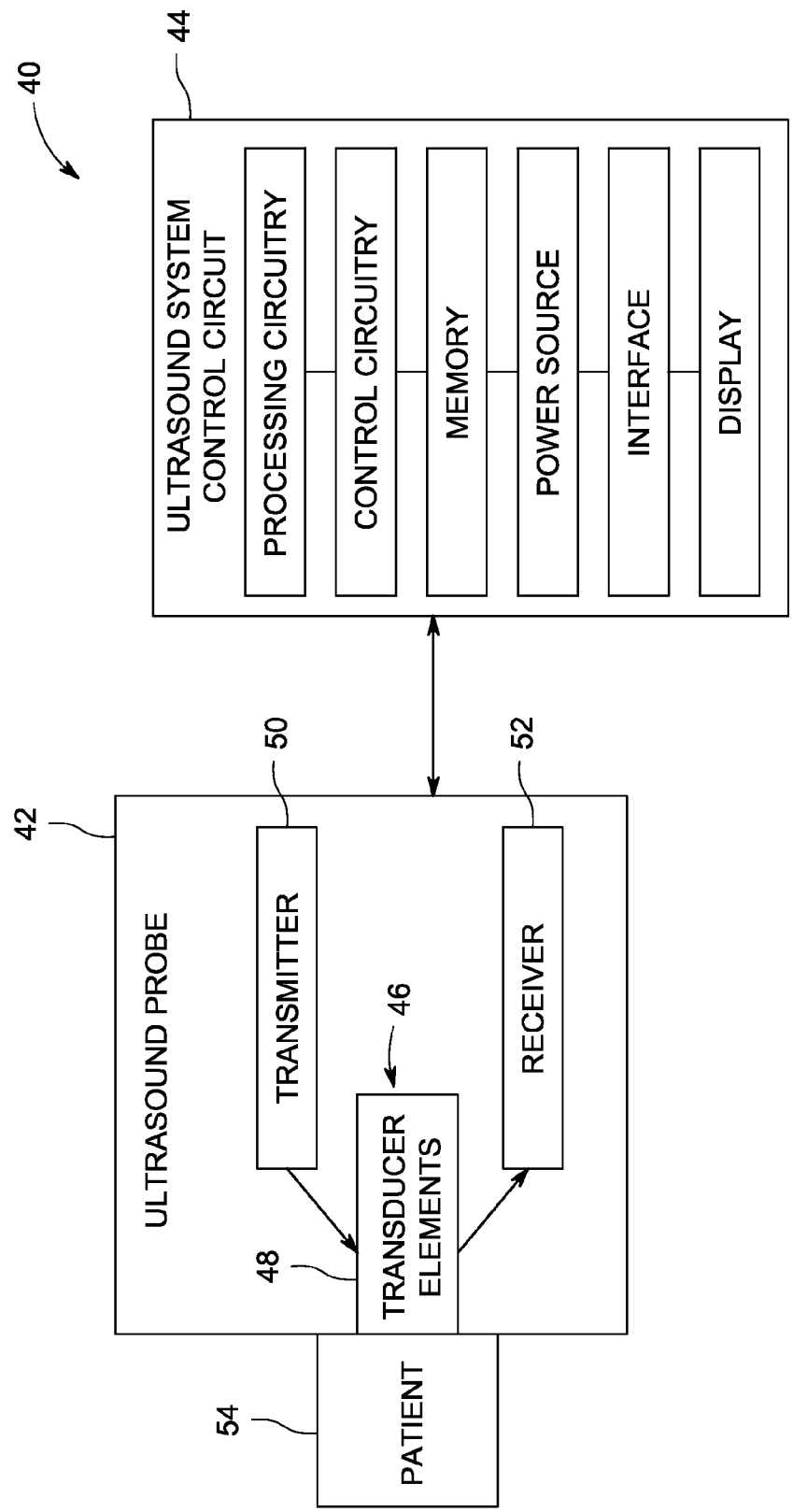
FIG. 2 is a diagrammatic illustration of an embodiment of an elastography system having an ultrasound imaging system configured to perform data acquisition, in accordance with an aspect of the disclosure.

During a typical data acquisition procedure with the ultrasound system 40 depicted in FIG. 2, the transducer array 46 is positioned on the patient 54, as described above. The transmitter 50 transmits ultrasound energy into the patient 54 via the transducer elements 48 of the transducer array 46, and the receiver 52 receives data from the array of transducers, wherein the received data corresponds to reflection signals returned from tissue interfaces within the patient 54 during data acquisition. The illustrated probe 42 includes transducer elements 48 that are configured to produce and detect ultrasound waves. Each individual transducer element 48 is generally capable of converting electrical energy into mechanical energy for transmission, as well as mechanical energy into electrical energy for receiving purposes. The transducers may be of any type suitable for use with diagnostic ultrasound, such as broad-bandwidth transducers, resonance transducers, and so forth. Any suitable configuration of transducer elements 46 and any suitable number of transducer elements 46 may be utilized. Any suitable number of transducer arrays 46 or sub-arrays may be utilized.

Once data is received by the console 44, the data can be transferred to the processing circuitry 16 for processing. The data can be processed and utilized to produce an image of the patient's tissue and/or to acquire displacement field data and/or reaction force data, in accordance with any suitable methods or procedures known in the art. Furthermore, the image and/or data can be displayed on the display 26 and/or an operator may interact with the image or data via the interface 24, as discussed above with respect to a general elastography system 10.

Figure 3:
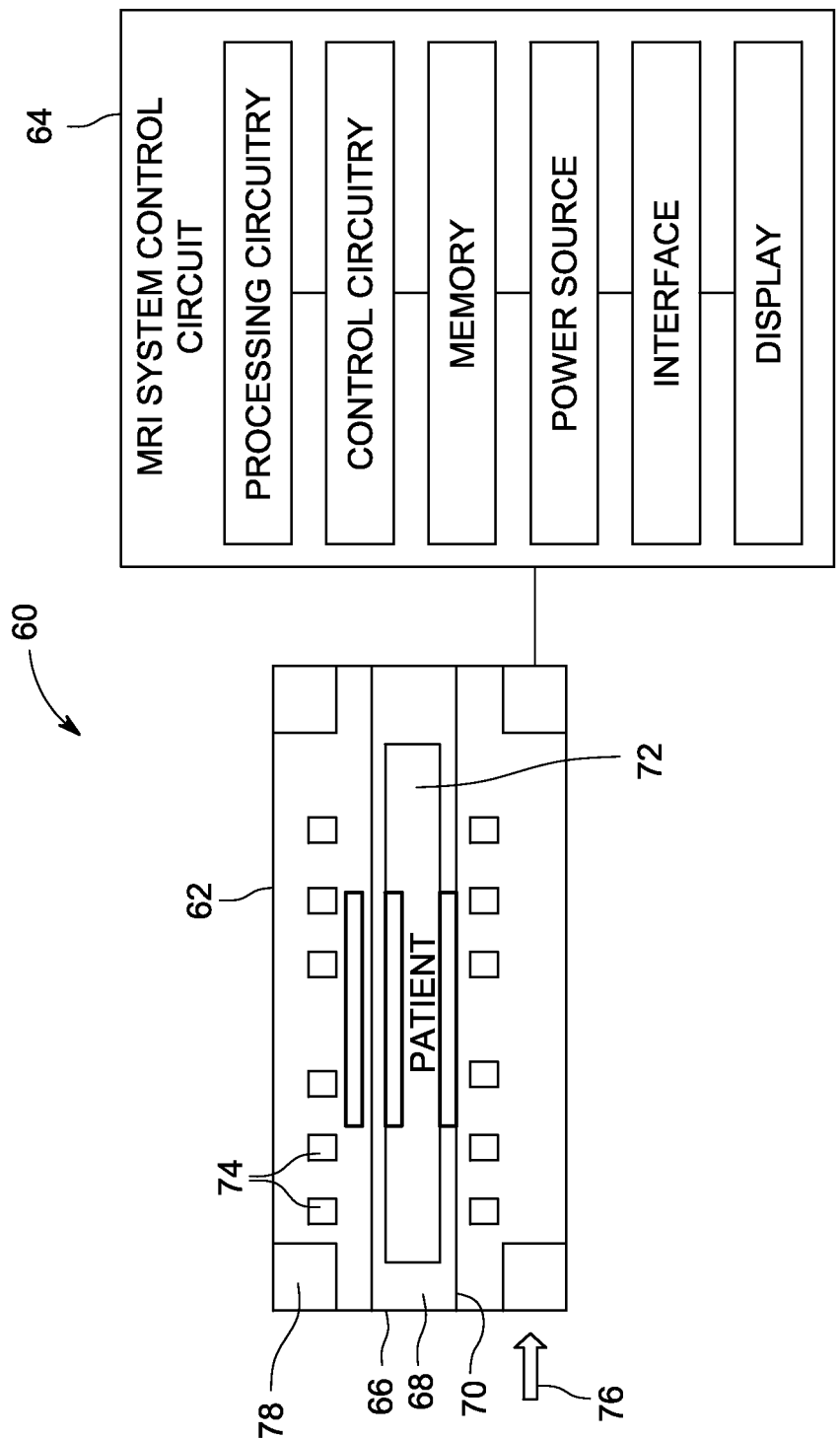
FIG. 3 is a diagrammatic illustration of an embodiment of an elastography system having a magnetic resonance imaging system configured to perform data acquisition, in accordance with an aspect of the disclosure.

In certain embodiments, the elastography system 10 can include an MRI system 60, such as the system depicted in FIG. 3. Referring to FIG. 3, an MRI system 60 is illustrated schematically as including a scanner 62 and a console 64. In the illustrated embodiment, the MRI system 60 includes a full body scanner 62 having a housing 66 through which a bore 68 is formed. A table 70 is moveable into the bore 68 to permit a patient 72 to be positioned therein for imaging selected anatomy within the patient. In the illustrated MRI system 60, the scanner 62 includes a series of coils 74 for producing controlled magnetic fields. The various coils of the MRI system 60 can be controlled by an external system control circuit 14, which can be located within the console 64, for example. In the illustrated embodiment, a main power 76 supply provides power to a primary coil 78.

Within the MRI system 60, the scanner 62 may be coupled to the console 64. The scanner 62 and console 64 may be within the same platform, or may be coupled together through a cable or wireless connection, for example. The console 64 may include a system control circuit 14, having components and functionality as described above with respect to elastography systems generally. For example, the system control circuit 14 can transmit control signals to the scanner 62 and/or can receive data from the scanner 62.

An MRI system 60, such as the one depicted in FIG. 3, generally operates by producing controlled magnetic fields and radio frequency pulses to excite specific material within a target area of the patient 72. In elastography procedures, vibrational energy may be applied to the patient's tissue concurrently with the controlled magnetic fields. The scanner 62 can sense signals emanating from the tissue, and the MRI system 60 can image displacements in the tissue resulting from the vibrational energy. Further, the MRI system 60 can generate displacement data and/or can create an image of the displacement field data. The image can be displayed on the display 26 and/or an operator may access the image via the interface 24, as discussed above with respect to a general elastography system 10. Any of a variety of suitable types of MRI systems may be employed as part of the presently discussed elastography systems and methods. Furthermore, while ultrasound and MRI systems may be particularly common in current elastography procedures, other data acquisition modalities and other imaging systems, such as computed tomography (CT) may be utilized, in accordance with aspects of the present disclosure.

As noted above, conventional elastography techniques provide only strain maps depicting the strain induced by application of a force or displacement. A major limitation with such strain maps is that they do not necessarily accurately reflect the modulus of the internal features. Furthermore, strain maps are particularly unsuitable for materials, such as soft tissue, that do not display linear stress-strain relationships. Accordingly, an elastography system that accounts for the nonlinear stress-strain relationship of soft tissue allows for generation of the more relevant modulus information (e.g., estimated modulus and/or map indicative of the relative modulus of different regions of the sample, or calculation of actual modulus values in some circumstances), the ability to better differentiate between tissue regions of different modulus, and the ability to identify small abnormalities, such as small tumors. Improved elastography systems and methods utilizing a nonlinear transfer function are discussed below.

A nonlinear transfer function suitable for use in the described systems and methods can be generated through any of a variety of means, as discussed further below. In some embodiments, the nonlinear transfer function may be based on the stress-strain relationship of the material, which may be determined by considering force and displacement data. Such force and displacement data may be acquired in a number of various ways. In some embodiments, the force and displacement may be measured by a data acquisition module 12, such as an ultrasound system 40. For example, the displacement applied to a material with an ultrasound probe 42 may be estimated, known, or measured. The reaction force on and/or within the material can be measured, such as by one or more transducers. The displacement and reaction force data can then be used to generate the nonlinear transfer function based on the material's stress-strain relationship.

Furthermore, in some embodiments, rather than generating the nonlinear transfer function by collecting force and displacement data from a sample, the nonlinear transfer function may be generated through the use of models or simulations, such as a model of a particular material. For example, a model of a particular soft tissue may be developed. The applied displacement and resulting reaction force can be determined through a forward solution. The stress and strain can be computed using the results of the forward solution, and a nonlinear transfer function can be generated based on the stress-strain relationship.

Additionally, the nonlinear transfer function may be generated based on displacement and force data obtained from a particular tissue region of a particular patient and utilized to provide modulus information for the same patient. In other embodiments, however, one or more nonlinear transfer functions may be generated based on empirical displacement and force data collected from one or more patients or tissue samples. As noted above, the one or more nonlinear transfer functions may also be generated through the use of models or simulations. In some implementations, the nonlinear transfer function may be generated by the processing circuitry 16 within the elastography system 10. Regardless of the techniques utilized to generate the nonlinear transfer function, the one or more nonlinear transfer functions may be stored in a memory, such as the memory 20 of the system control circuit 14. The one or more stored nonlinear transfer functions may be available for access and/or selection by an operator, external computer, or processing circuitry 16 for application to displacement data, for example. Furthermore, in some embodiments, the one or more nonlinear transfer functions may be classified based on characteristics of the nonlinear transfer function. The one or more nonlinear transfer functions may be classified with respect to a particular tissue type (such as, breast tissue or liver tissue, for example), a particular patient, or a particular type of patient (such as, based on certain physiological, anatomical, or health issues, or based on patient demographics, such as age, sex, body mass index, and so forth), for example. In certain embodiments, classification may allow a user or system to more easily select a suitable nonlinear transfer function by inputting selection criteria or browsing through various classes of available nonlinear transfer functions, for example.

Figure 4:
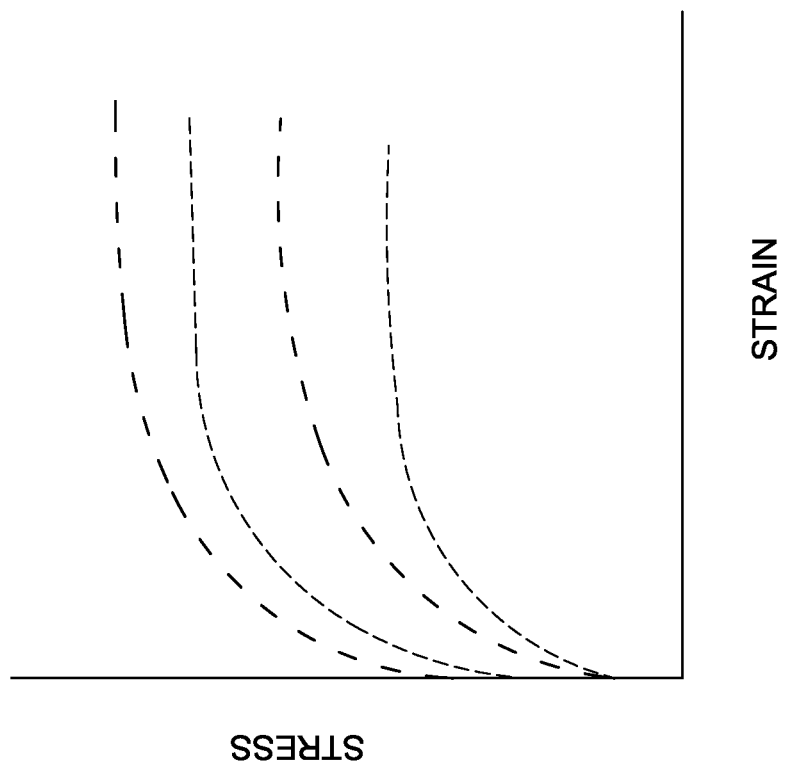
FIG. 4 depicts a graph illustrating suitable nonlinear transfer functions, in accordance with an aspect of the disclosure.

Described above are some examples of the ways in which the nonlinear transfer function may be generated. Additionally, any of a variety of plasticity curves that relate the stress to the strain of the material may be suitable for transforming displacement data and/or maps (e.g., a strain map), in accordance with embodiments discussed herein. In some embodiments, an appropriate curve may have a secant modulus measured at every point of the curve increases from a very high stiff value to a very low value, including zero. In other words, a curve having a steep slope at low values of strain, and a less steep slope at higher values of strain, along with a generally concave downward shape may be appropriate for transforming the data. Due to the shape of such curves, regions of low deformation may be enhanced, thus providing for the identification of smaller tumors or other small regions of relatively high stiffness, for example. Several embodiments of suitable curves are illustrated in FIG. 4. In view of this, a nonlinear transfer function may also be generated by assuming or selecting a curve within this broad spectrum of suitable curves. A mathematical description of these curves (in which σ is stress and ε is strain) is: σ=f(ε) such that $$\frac{\partial \sigma}{\partial \varepsilon} > 0 \text{ and } \frac{\partial^2 \sigma}{\partial \varepsilon^2} < 0.$$

Figure 5:
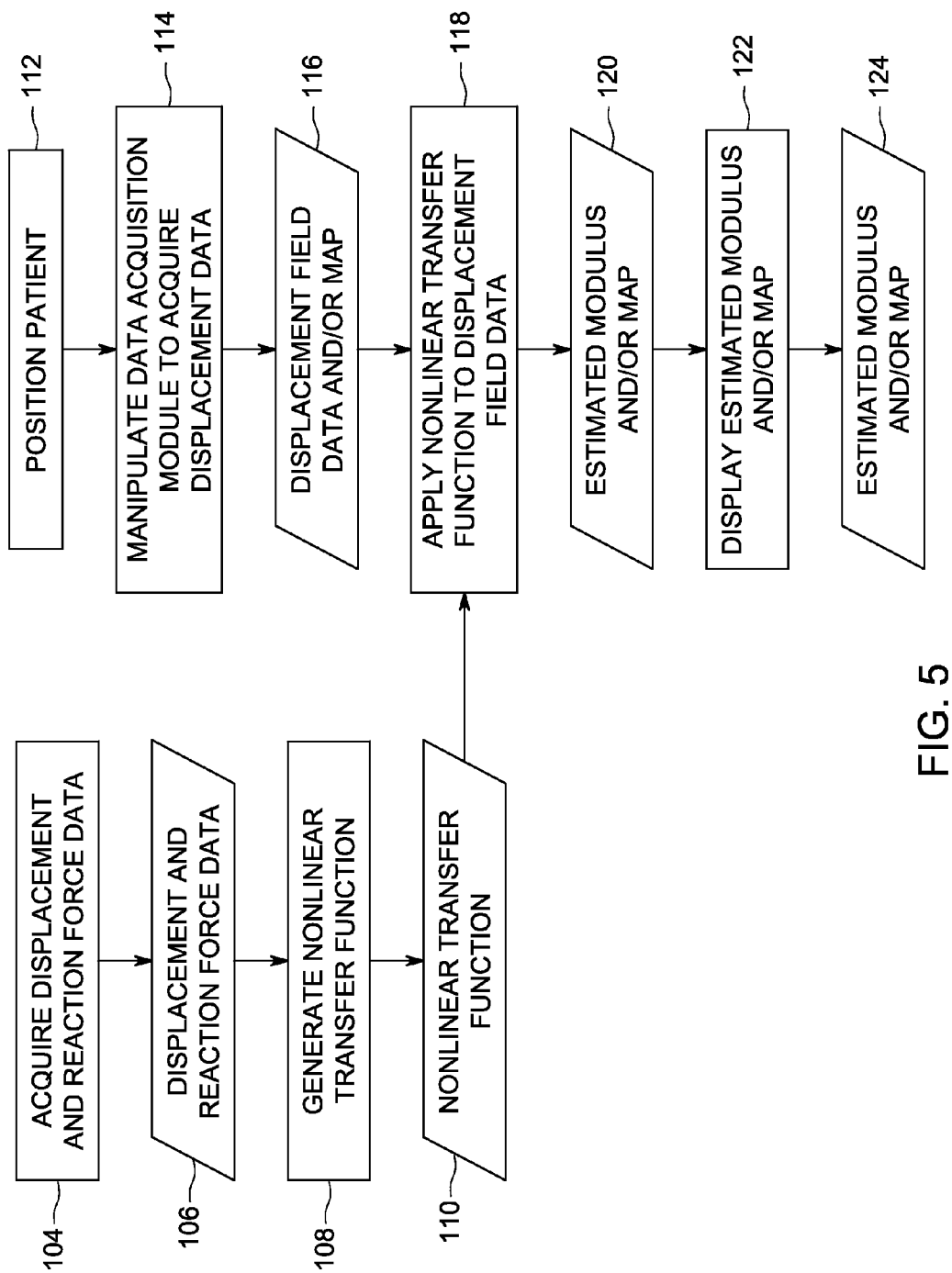
FIG. 5 depicts a flowchart describing one method for implementing a nonlinear elastography procedure, in accordance with an aspect of the disclosure.

One embodiment of a method for implementing a nonlinear elastography procedure is depicted in the flowchart of FIG. 5. As shown in the provided flowchart, in step 104, displacement and resulting reaction force data 106 may be acquired to generate the nonlinear transfer function. As discussed above, such displacement and resulting reaction force data 106 may be acquired in any of a variety of ways. For example, the displacement and resulting reaction force data 106 may be acquired by using an ultrasound system 40 to apply a known displacement to a material, such as via probe 42, and measuring the resultant force. Such measurements can be collected by one or more transducers positioned directly on or within the material, or located on or within an ultrasound probe 42, for example. In other embodiments, the displacement and reaction force data 106 used to generate the nonlinear transfer function may be acquired through the use of models or simulations, as described above. Regardless of the methods for acquiring the displacement and resulting reaction force data 106, once the displacement and reaction force data 106 are obtained, step 108 provides for generation of a nonlinear transfer function 110 based on the material's stress-strain relationship. In one implementation the nonlinear transfer function 110 can be generated by the processing circuitry 16 within the elastography system 10. In some embodiments, the nonlinear transfer function 110 may be stored in a memory, such as in the memory 20 of the system control circuit 14, for example.

In accordance with the embodiment illustrated in FIG. 5, the generated nonlinear transfer function 110 may then be used to create an estimated modulus and/or map, as described in detail below. In particular, a patient may be positioned in such a way as to allow an imaging system to access the patient in step 112. In step 114, any suitable data acquisition module 12, such as an ultrasound probe 42, may be manipulated in order to acquire data for a particular region of tissue. The system control circuit 14 can then process the raw data to generate displacement field data and/or map 116. The displacement field data and/or map 116 may generally be any data or map indicative of the displacement or strain within the material. For example, the acquired displacement field data and/or map 116 may be a dimensionless strain map. Additionally, the displacement field data and/or map 116 need not include actual numerical displacement values. Rather, the displacement field data and/or map 116 may only reflect the relative displacement or relative strain within different regions of the material. Regardless of the particular form of the acquired displacement field data and/or map 116, in some embodiments, the displacement field data and/or map 116 can additionally be displayed on a display 26, or can be processed, stored, or communicated to any suitable output device, including those described above. In some embodiments, the displacement field data and/or map 116 can be stored, such as in the memory 20 of the system control circuit 14.

After the displacement field data and/or map 116 is acquired, the nonlinear transfer function 110 may be applied to the displacement field data and/or map 116 in step 118. As a result, an estimated modulus and/or map 120 is generated. For example, when the nonlinear transfer function 110 is applied to the displacement field data and/or map 116, an estimated modulus and/or map 120 reflecting the relative modulus of the different regions of the material may be created. The estimated modulus and/or map 120 can be displayed on a display, in step 122, allowing a user to observe the displayed estimated modulus and/or map 124. Additionally, the estimated modulus and/or map 120 can be processed, stored, or communicated to any suitable output device.

As described above, applying the nonlinear transfer function 110 to displacement data and/or map 116 (e.g., a strain map) may provide an estimated modulus and/or map 120 depicting the relative modulus of regions within the sample. However, in some embodiments, application of the nonlinear transfer function 110 may allow for the generation of actual modulus values. The generation of actual modulus values is possible where the data acquisition module 12, or some other suitable input mechanism, is used to acquire the actual value of a force (such as, for example, the force applied to the tissue surface by the probe 42, which may be determined by a transducer positioned on the surface of the patient's tissue) and the actual value of the corresponding displacement. Applying the nonlinear transfer function 110 to such actual force and displacement values allows the actual modulus value of the target tissue to be calculated, in some embodiments. In other words, the system 10 may be configured to acquire a value of an applied force and a value of a corresponding displacement and to apply the nonlinear transfer function 110 to the acquired values to calculate modulus values representative of the stiffness of the different regions of the material. Such modulus values may provide additional information regarding the inhomogeneities within the various regions of the material (for example, certain modulus values may indicate the presence of a malignant tumor while certain different modulus values may indicate the presence of a benign tumor).

While the steps for generating the nonlinear transfer function 110 and the steps for acquiring the displacement field data and/or map 116 are treated sequentially above, generation of the nonlinear transfer function 110 and acquisition of the displacement field data and/or map 116 may occur in a substantially simultaneous manner. In some embodiments, the displacement and reaction force data 106 used to generate the nonlinear transfer function 110 and the displacement field data and/or map 116 may both be acquired during a single elastography session, or even during a single data acquisition step. In other embodiments, the nonlinear transfer function 110 may be generated before or after positioning the patient 112 and/or manipulating the data acquisition module 114. For example, the nonlinear transfer function 110 may be determined as an initial step, based on empirical data or data collected during a patient's separate office visit, for example.

Figure 6:
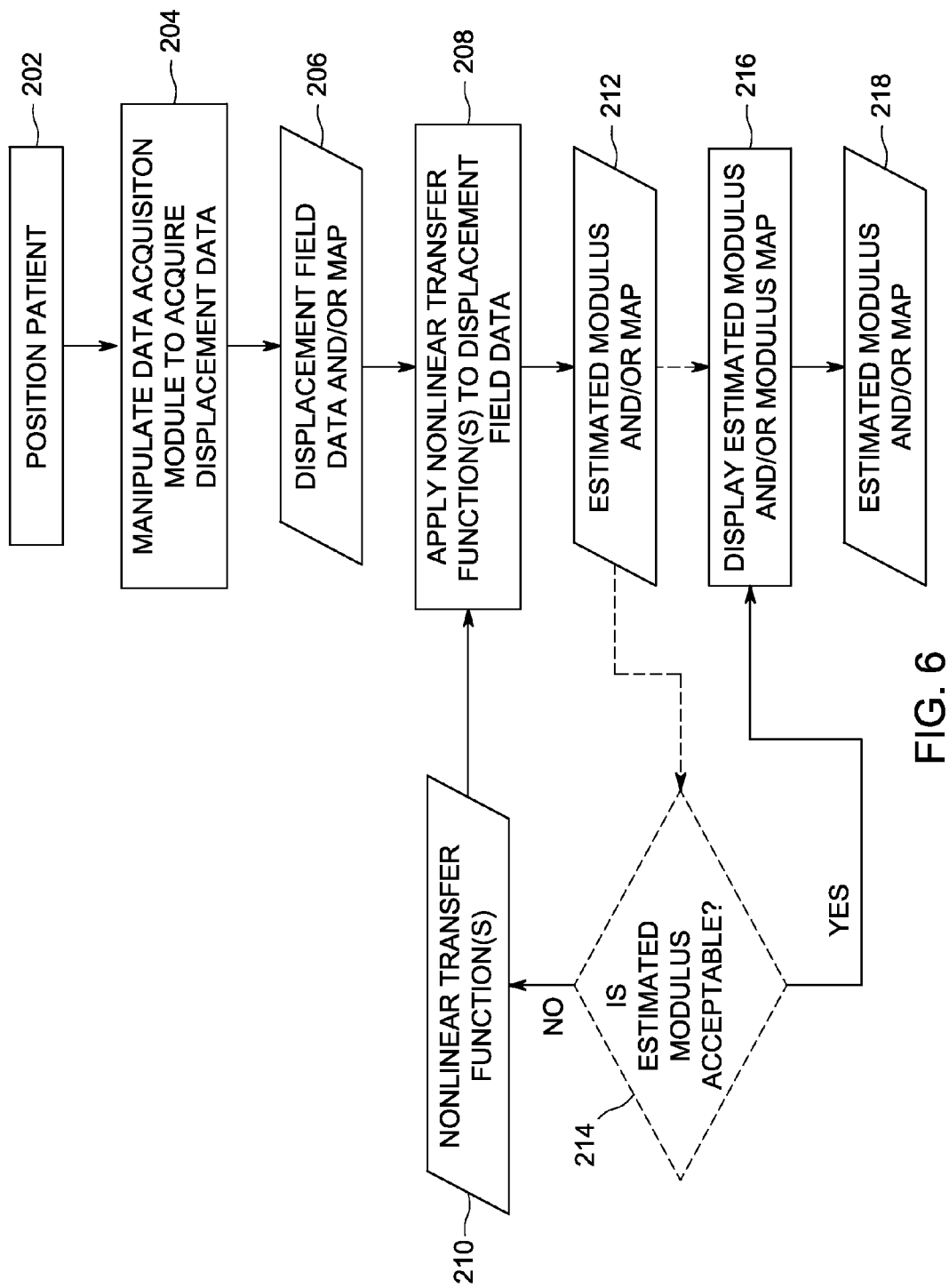
FIG. 6 depicts a flowchart describing one method for implementing a nonlinear elastography procedure comprising an optional optimization step, in accordance with an aspect of the disclosure.

FIG. 6 illustrates another embodiment of the described elastography systems and methods. The method depicted in FIG. 6 differs from FIG. 5 in that, the nonlinear transfer function is not necessarily generated based on acquired displacement and force data as part of the elastography method, but rather, a suitable nonlinear transfer function is stored or otherwise inputted into the system, as described in more detail below. Additionally, FIG. 6 illustrates an optional optimization step that may be implemented in generating an estimated modulus and/or map, as discussed in detail below. Specifically, in the embodiment of FIG. 6, in step 202, a patient is initially positioned to allow a data acquisition module 12 to access the patient. Any suitable data acquisition module 12 or components therein, such as an ultrasound probe 42, may be manipulated in order to acquire displacement data for a particular region of tissue in step 204. The system control circuit 14 can then process the raw data to generate displacement field data and/or map 206. As discussed above with respect to FIG. 5, the displacement field data and/or map 206 may be any data or map indicative of the displacement or strain within the region. For example, the acquired displacement field data and/or map 206 may be a dimensionless strain map. In some embodiments, the displacement field data and/or map 206 can be displayed on a display 26, and can be processed, stored, or communicated to any suitable output device, including those described above. In some embodiments, the displacement field data can be stored, such as in the memory 20 of the system control circuit 14.

After the displacement field data and/or map 206 are acquired, a nonlinear transfer function 210 may be applied to the displacement field data and/or map 206 in step 208 of the illustrated embodiment. Application of the nonlinear transfer function 210 to the displacement field data and/or map 206 may provide an estimated modulus and/or a map 212, as described above with respect to FIG. 5. In the illustrated embodiment, the nonlinear transfer function 210 may be a preset function stored or programmed into the elastography system 10. For example, the nonlinear transfer function 210 may have been previously or separately determined based on force or displacement data acquired from a patient, a model or simulation, or empirical data based on patient studies or samples. Alternatively, the nonlinear transfer function 210 may be assumed to be any suitable plasticity curve having the characteristics described above.

In certain implementations, one or more nonlinear transfer functions 210 may be stored or programmed into the elastography system 10. Indeed, in some embodiments a database of a plurality of nonlinear transfer functions 210 may be provided. In some embodiments, a particular nonlinear transfer function 210 may be selected from the preset functions for application to the acquired displacement field data and/or map 206. A suitable nonlinear transfer function 210 may be selected by an operator, may be automatically selected by the elastography system 10, or may be selected by the elastography system 10 based on various inputs or factors (such as, for example, patient factors, tissue type, measured or known tissue characteristics, etc.). Various alternatives for storing, selecting, and/or applying a nonlinear transfer function 210 are also envisioned.

Once the estimated modulus and/or map 212 is obtained, an optional optimization step 214 may be carried out, in accordance with certain embodiments. For example, the system control circuit 14 may be configured to determine whether the estimated modulus and/or map 212 is acceptable (such as, for example, whether the modulus map has an acceptable clarity). In some embodiments, the system control circuit 14 may be configured to process and analyze the displacement data and/or map 206 and the estimated modulus and/or map 212 to determine whether the nonlinear transformation suitably improved the clarity or contrast of the displacement data and/or map 206, for example. In some embodiments, the system control circuit 14 may be configured to apply two or more nonlinear transfer functions 210 to a set of displacement data 206 in order to carry out two or more transformations in parallel, and the system control circuit 14 may be further configured to select a preferred estimated modulus and/or map 216 based on relative clarity, for example. In such embodiments, the preferred estimated modulus and/or map 216 may be displayed on a display 26 or communicated to an external device. Although FIG. 6 illustrates that the optional optimization step may be completed by the system after the estimated modulus and/or map is determined, in some embodiments the optional optimization step may be completed by an operator after the estimated modulus and/or map is displayed. For example, the estimated modulus and/or map 212 may be provided to an operator via an interface 24 or display 26 in the system control circuit 14. The operator may evaluate the estimated modulus and/or map 212 to determine whether the estimated modulus and/or map 212 is acceptable. The operator may, for example, analyze the clarity or contrast of the estimated modulus and/or map 212 to determine acceptability.

In step 216, the estimated modulus and/or map 212 can be provided through an interface 24 or displayed on a display 26, if the estimated modulus and/or map 212 is determined to be acceptable. However, if the estimated modulus and/or map 212 is determined to be unacceptable, a different or modified nonlinear transfer function 210 may be applied to the displacement field data and/or map 206. In some instances, a new nonlinear transfer function 210 may have to be generated. In some embodiments, however, a different nonlinear transfer function 210 may be selected from the programmed functions within the system control circuitry 14. In yet other embodiments, a different nonlinear transfer function 210 may be provided by an operator or provided by an external device, for example.

Following generation, selection, or provision of a new or different nonlinear transfer function 210, step 208 may be repeated as the new or different nonlinear transfer function 210 is applied to the displacement field data and/or map 206. The new estimated modulus and/or map 212 may then be fed through the optional optimization step 214 once more. These steps may be repeated until acceptable estimated modulus and/or map is achieved. Once the estimated modulus and/or map 212 is determined to be acceptable, the estimated modulus and/or map 212 may be displayed on the display 26 or provided to an operator via an interface 24, for example. In certain embodiments, additional or alternate optimization mechanisms may be in place. For example, an operator or a system may first assess whether acquired displacement field data and/or map 206 is acceptable prior to applying the nonlinear transfer function 210 in step 208. In some instances, it may be necessary to return to steps 202 and/or 204 to repeat measurement steps to acquire acceptable displacement field data and/or map 206. Repeating step 204 to acquire displacement data and/or map 206 may be necessary where image quality is poor, or where multiple nonlinear transfer functions 210 have been applied without achieving acceptable estimated modulus and/or maps 212, for example.

Figure 7B:
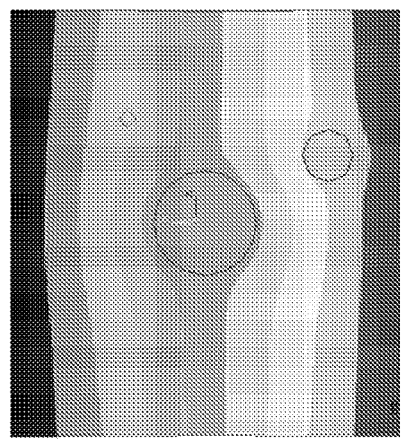
FIG. 7B depicts a model of a displacement field of human soft tissue having three inclusions, in accordance with an aspect of the disclosure.
Figure 7D:
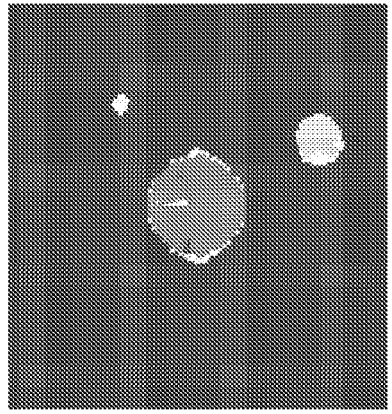
FIG. 7A depicts a model of human soft tissue having three inclusions, in accordance with an aspect of the disclosure.
FIG. 7C depicts a sample strain map of human soft tissue having three inclusions, as generated by conventional elastography techniques; and, FIG. 7D depicts a sample modulus map of human soft tissue having three inclusions, in accordance with an aspect of the disclosure.
Figure 7A:
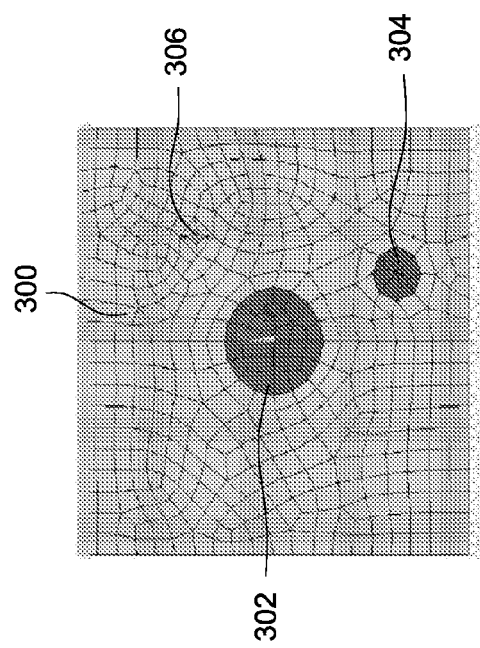
Figure 7C:
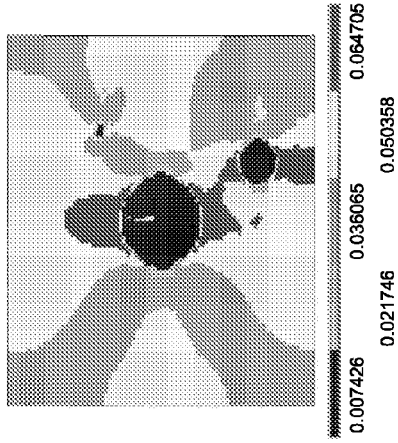

FIGS. 7A-7D illustrate at least some of the benefits of the nonlinear elastography systems and methods described in the present disclosure. Although FIGS. 7A-7D are based on a computer generated model, the figures show that the presently disclosed systems and methods may provide improved detection of abnormalities, such as tumors embedded within tissue, for example. FIG. 7A depicts a model of soft tissue 300 with tumors of three different sizes and moduli embedded therein. In the illustrated experimental model, the large tumor 302 has a modulus of 0.333 MPa, the medium tumor 304 has a modulus of 1.0 MPa, the small tumor 306 has a modulus of 0.333 MPa, and the soft tissue 300 has a modulus of 0.1 MPa. FIG. 7B shows a displacement field map obtained via forward solution. As shown, the displacement field of the soft tissue 300 is most affected by the presence of the large tumor 302. However, the small tumor 306 only creates a very small change in the displacement field, which illustrates that displacement data and/or maps alone do not provide acceptable identification of small tumors. In fact, FIG. 7C shows a strain map of the soft tissue 300. Not only is the small tumor 306 unclear, but the differentiation between regions of different modulus is poor. However, upon application of nonlinear transfer function as described herein, a modulus map 400 such as the map shown in FIG. 7D may be generated. As shown, application of the nonlinear transfer function in accordance with the present disclosure has the effect of amplifying the contrast between regions of different modulus. The concavity of the curves as described above with reference to FIG. 5, also provides for particular enhancement of low deformation regions. As illustrated, all three tumors are visible in the model's modulus map 400. Furthermore, the modulus map 400 provides improved differentiation between regions of different modulus, including improved differentiation between the tumors of different modulus, which may be important for the identification of malignant versus benign tumors, for instance. Additionally, the modulus map 400 provides improved identification of the small tumor 306, as well as overall improved image clarity and contrast, as compared to the strain map of FIG. 7C. As illustrated, suitable nonlinear transfer functions described in the present disclosure generally have the effect of amplifying the contrast between tissues of different modulus, resulting in improved image contrast and clarity.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A method for elastography, the method comprising:
  applying a displacement to a surface of a volume of a tissue;
  measuring a resulting reactive force on the surface or within the volume of the tissue;
  generating a nonlinear transfer function based on a relationship between the applied displacement and measured resulting reactive force, wherein the nonlinear transfer function has a slope that decreases between a relatively low value of strain and a higher value of strain; and
  applying the nonlinear transfer function to a map indicative of strain within the volume of the tissue to generate a modulus map providing information about regions of different stiffness within the volume of the tissue.

2. The method of claim 1, wherein the displacement is applied and the resulting reactive force is measured using an ultrasound system.

3. The method of claim 1, wherein the displacement is applied and the resulting reactive force is measured using a model of the tissue.

4. The method of claim 1, further comprising storing the nonlinear transfer function in a memory and accessing the nonlinear transfer function from the memory for application to the map indicative of strain within the volume of the tissue.

5. The method of claim 4, comprising classifying, within the memory, the nonlinear transfer function with respect to a tissue type to facilitate selection of the nonlinear transfer function from a plurality of stored nonlinear transfer functions for application to the map indicative of strain within the volume of the tissue.

6. The method of claim 1, further comprising storing the nonlinear transfer function in a memory and classifying the nonlinear transfer function based on one or more characteristics of the nonlinear transfer function.

7. A system configured to determine mechanical properties of a material having regions of different stiffness, the system comprising:
  an imaging system configured to acquire displacement field data for a volume of the material;
  a circuit configured to access one or more nonlinear transfer functions, wherein the one or more nonlinear transfer functions have a generally downward concave shape; and
  a processor configured to apply at least one nonlinear transfer function to the acquired displacement field data to generate a modulus map that provides information about the regions of different stiffness within the volume of the material.

8. The system of claim 7, wherein the imaging system comprises an ultrasound system.

9. The system of claim 7, wherein the imaging system comprises a magnetic resonance imaging system.

10. The system of claim 7, wherein the nonlinear transfer functions are based on a stress-strain relationship of the material.

11. The system of claim 7, further comprising a memory storing the one or more nonlinear transfer functions for access by the circuit.

12. The system of claim 11, wherein each of the one or more stored nonlinear transfer functions are classified based on one or more characteristics of the nonlinear transfer function.

13. The system of claim 7, further comprising a display suitable to display the modulus map.

14. The system of claim 7, wherein the system is configured to acquire a value of an applied force and a value of a corresponding displacement for the volume of the material and to apply the nonlinear transfer function to the acquired values to calculate modulus values representative of the stiffness of the regions of different stiffness within the volume of the material.

15. A method for determining mechanical properties of a material having regions of different stiffness, the method comprising:
  applying a force to a surface of a volume of the material to induce a displacement within the volume of the material;
  measuring the displacement within the volume of the material to generate a displacement field map;

accessing one or more nonlinear transfer functions, wherein the one or more nonlinear transfer functions has a generally downward concave shape; and applying at least one nonlinear transfer function to the displacement field map to generate a modulus map providing information about the regions of different stiffness within the volume of the material.

16. The method of claim 15, further comprising:

determining whether the modulus map has an acceptable clarity; and applying a different nonlinear transfer function if the modulus map is determined not to have acceptable clarity.

17. The method of claim 16, wherein determining whether the modulus map has the acceptable clarity is carried out by an operator.

18. The method of claim 16, wherein determining whether the modulus map has the acceptable clarity is carried out by a system circuitry within an elastography system.

19. The method of claim 15, wherein the force is applied and the displacement is measured using an ultrasound system.

20. The method of claim 15, wherein a value of the applied force and a value of the induced displacement within the volume of the material is acquired and the nonlinear transfer function is applied to the acquired values of the applied force and the induced displacement to calculate modulus values representative of the stiffness of the regions of different stiffness within the volume of the material.

* * * * *